United States Patent
Kumta et al.

(10) Patent No.: US 12,105,087 B2
(45) Date of Patent: Oct. 1, 2024

(54) MULTI-ARRAY IMPEDIMETRIC BIOSENSORS FOR THE DETECTION OF CONCUSSION AND TRAUMATIC BRAIN INJURIES

(71) Applicant: UNIVERSITY OF PITTSBURGH—OF THE COMMONWEALTH SYSTEM OF HIGHER EDUCATION, Pittsburgh, PA (US)

(72) Inventors: Prashant Kumta, Pittsburgh, PA (US); Mitali Patil, Pittsburgh, PA (US); David Okonkwo, Pittsburgh, PA (US); Robert Kormos, Pittsburgh, PA (US)

(73) Assignee: UNIVERSITY OF PITTSBURGH-OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 732 days.

(21) Appl. No.: 16/467,116

(22) PCT Filed: Dec. 11, 2017

(86) PCT No.: PCT/US2017/065528
§ 371 (c)(1),
(2) Date: Jun. 6, 2019

(87) PCT Pub. No.: WO2018/107143
PCT Pub. Date: Jun. 14, 2018

(65) Prior Publication Data
US 2019/0317089 A1    Oct. 17, 2019

Related U.S. Application Data

(60) Provisional application No. 62/432,119, filed on Dec. 9, 2016.

(51) Int. Cl.
| | |
|---|---|
| *G01N 33/543* | (2006.01) |
| *C07K 16/18* | (2006.01) |
| *G01N 33/68* | (2006.01) |
| *A61B 5/00* | (2006.01) |
| *A61B 5/145* | (2006.01) |
| *G01N 27/00* | (2006.01) |

(52) U.S. Cl.
CPC ....... *G01N 33/54373* (2013.01); *C07K 16/18* (2013.01); *G01N 33/5438* (2013.01); *G01N 33/6893* (2013.01); *A61B 5/145* (2013.01); *A61B 5/4064* (2013.01); *A61B 2562/0285* (2013.01); *G01N 27/00* (2013.01); *G01N 2800/2871* (2013.01)

(58) Field of Classification Search
None
See application file for complete search history.

(56) References Cited

U.S. PATENT DOCUMENTS

| | | |
|---|---|---|
| 2012/0244547 A1 | 9/2012 | Mazzari et al. |
| 2014/0011691 A1 | 1/2014 | Sierks et al. |
| 2014/0255952 A1 | 9/2014 | Kumta et al. |
| 2015/0085249 A1 | 3/2015 | Abreu |

FOREIGN PATENT DOCUMENTS

WO    2014006394 A2    1/2014

OTHER PUBLICATIONS

North et al., Rapid Analytical Methods for On-Site Triage for Traumatic Brain Injury, Annu. Rev. Anal. Chem. 2012, 5, pp. 35-56. (Year: 2012).*
Martin-Fernandez et al., Vertically aligned multi-walled carbon nanotube growth on platinum electrodes for bio-impedance applications, Microelectronic Engineering 86, 2009, pp. 806-808. (Year: 2009).*
Arya et al. "Effects of the electrode size and modification protocol on a label-free electrochemical biosensor," Langmuir, Jun. 4, 2013 (Jun. 4, 2013), vol. 29, No. 22, pp. 6770-6777. entire document.
Kaushik et al. "Nano-biosensors to detect beta-amyloid tor Alzheimer's disease management," Biosensors and Bioelectronics, Jun. 15, 2016 (Jun. 15, 2016), vol. 80, pp. 273-287. entire document.

* cited by examiner

*Primary Examiner* — Gary Counts
(74) *Attorney, Agent, or Firm* — Carol A. Marmo; Eckert Seamans Cherin & Mellott, LLC

(57) ABSTRACT

The invention includes an ex-situ biosensors that impedimetrically detect one or more target biomarkers of brain injury or disease in a bodily fluid sample derived from a patient. The biosensors include a multi-array of vertically aligned platinum wires having immobilized thereon antibody and/or aptamer that specifically and selectively bind to the one or more target biomarkers. An electrochemical impedance signal is generated, and a change in electrochemical impedance is indicative of the presence of the one or more target biomarker(s) in the bodily fluid sample. The biosensors are point-of-care, on-demand devices useful in a medical and domestic environment.

6 Claims, No Drawings

MULTI-ARRAY IMPEDIMETRIC BIOSENSORS FOR THE DETECTION OF CONCUSSION AND TRAUMATIC BRAIN INJURIES

CROSS-REFERENCE TO RELATED APPLICATIONS

This application is a U.S. National Stage Application under 35 U.S.C. § 371 of PCT International Application No. PCT/US2017/065528, filed on Dec. 11, 2017, entitled "Multi-Array Impedimetric Biosensors for the Detection of Concussion and Traumatic Brain Injuries" which claims priority under 35 U.S.C. § 119(e) to U.S. Provisional Patent Application Ser. No. 62/432,119, filed Dec. 9, 2016, entitled "Multi-Array Impedimetric Biosensors for the Detection of Concussion and Traumatic Brain Injuries", which are herein incorporated by reference.

FIELD OF THE INVENTION

The invention relates to multi-array, antibody- and/or aptamer-based biosensors for impedimetric detection in a biological sample of one or more target biomarkers of interest, such as, Tau proteins and other related biomarkers, such as Glial Fibrilar Acidic Protein and Ubiquitin C-Terminal Hydrolase L1, which are predictive of brain concussion and traumatic brain injury, and diagnosis as well as prognosis of neurodegenerative diseases. More particularly, the invention relates to generation of antibody- and/or aptamer-based sensor devices to provide on-demand, point-of-care screening, analysis and results.

BACKGROUND

There are various antibody-based biosensors that are known in the art. Antibodies are oligonucleotide sequences that bind to their target with high affinity and specificity. The use of aptamer-based biosensors is more recent and, in general, not as well known. Aptamers are synthetic oligonucleotide sequences that are synthesized to bind to their target with high affinity and specificity. The synthetic process of producing aptamers ensures the following properties and characteristics: high stability in various environments, long shelf lives, and minimal batch-to-batch variation, while maintaining their affinity and specificity. The aptamer-based biosensor can provide a stable system that may be more easily translated to a medical device. Furthermore, the small size and lack of hydrophobic core in aptamers can prevent aggregation, which has been found to be problematic in antibodies.

Synthesis and generation of an impedimetric device requires the use of the antibody and/or aptamer in conjunction with a conducting material interface. The selection of the conducting material interface is based on desired properties, such as its chemically and electrochemically inert noble metal status, high electrical conductivity, affinity towards immobilizing agents, and biocompatibility. Often conducting materials such as platinum electrodes or nanoparticles are used in tandem with other material interfaces, such as, carbon nanotubes/nanocomposites, graphene, chitosan, silica, polymers, or gold.

The biomarkers of interest in diagnosing the risk and prevalence of concussion and traumatic brain injury (TBI) are Tau proteins and other related biomarkers, such as, Glial Fibrilar Acidic Protein (GFAP) and Ubiquitin C-Terminal Hydrolase L1 (UCH-L1). It has been shown that these biomarkers increase when a patient undergoes a TBI. Therefore, tailoring biosensors to detect these target biomarkers is of particular interest.

Tau proteins are microtubule-associated proteins (MAP) and are mostly located in the neurons of the central nervous system (CNS). The main function of Tau proteins is to provide stability and flexibility to microtubules (tubular polymers of tubulin that are a main component of the cytoskeleton) in the axons, especially the distal portion of the axons. The Tau proteins interact with tubulin to promote assembly of tubulin into microtubules, thus providing stability to the microtubules, which in turn maintain cellular structure along with microfilaments and intermediate filaments. One of the main mechanisms in which Tau controls microtubule stability is through phosphorylation of the Tau protein. However, hyperphosphorylation of the Tau protein can result in the formation of neurofibrillary tangles (NFTs), thus stimulating the onset and progression of numerous neurodegenerative diseases, especially Alzheimer's disease. In addition, Tau has been implicated as a biomarker of axonal damage after acute damage to the brain such as stroke, concussion, and subarachnoid hemorrhage, and the level of these biomarkers correlate with the severity of brain damage. Other high value, blood-based biomarker candidates for assessing TBI are GFAP and UCH-L1.

Current methods of assessing Tau proteins are to assess the levels of Tau in cerebrospinal fluid (CSF), which is a fluid that is within direct contact with the brain parenchyma and thus, allows for the monitoring of biochemical changes in the CNS. However, the method for withdrawing CSF samples for further analysis involves an expensive and invasive lumbar puncture, making it difficult to implement routine testing of Tau in CSF. Therefore, a minimally invasive technique for the detection of Tau proteins is required to assess changes in Tau levels for brain injury or neurodegenerative diseases.

Various existing biosensor-based technologies are primarily based on fluorescent-immunoassays that require fluorescently-labeled antibodies and a bench-top analyzer for the fluorescent assay. Common immunoassays include membrane-based immunoassays such as lateral flow devices (LFD) and enzyme-linked immunosorbent assays (ELISAs). These tests are highly dependent on the use of fluorescently labeled antibodies and spectrophotometers for analysis of fluorescence levels. The assays are typically conducted in laboratories and require significant pre-analytical time and analytical time, which increases turn-around time. In addition, many of these devices require a greater volume of blood than a typical glucose detector.

Current systems used for detecting mild TBI (mTBI) or severe TBI (sTBI) and concussion, such as, magnetic resonance imaging (MRI) or computer aided tomography (CAT) scans require expensive equipment and trained, highly-skilled personnel for proper functioning. In addition, systems focused on blood work, such as, the aforementioned LFDs or ELISAs, require bench-top analyzers, extensive pre-analytical time, and often require inordinate amount of time including many days for paperwork processing. Thus, there is a need to design a multi-array biosensor including antibodies and/or aptamers to serve as point-of-care devices that can be utilized to assess levels of brain concussion-related markers in the blood at the patient's bedside within a matter of mere minutes.

In general, there is a lack of standard diagnostic methods. Further, turnover of processing blood samples in hospitals and laboratories is frequently slow, and common diagnostic methods are expensive, time-consuming and invasive, requiring the patient to be tested in a medical facility and requiring the results to be obtained by skilled and trained personnel. These circumstances do not promote routine testing. Thus, there is a need for the development of improved impedimetric sensors capable of providing one or more of efficient, early, convenient (e.g., point-of-care, on-demand), inexpensive, rapid, minimally or non-invasive, and accurate impedimetric detection and screening of a target biomarker or multiple target biomarkers simultaneously, and a diagnosis or prognosis of concussion and traumatic brain injury or disease risk in patients. These circumstances will provide preventative medication and therapeutic treatment for favorable outcomes. Moreover, the sensing, detection and screening methods may be utilized outside the confines of a hospital or other medical facility, e.g., in a domestic setting, such as, a patient's home.

SUMMARY OF THE INVENTION

In one aspect, the invention provides a portable, ex-situ system to impedimetrically detect one or more target biomarkers related to brain injury or disease in a patient bodily fluid sample. The system includes a conducting material interface having a surface, and a biological sensor agent applied to the surface of the conducting material interface. The biological sensor agent includes an immobilization agent, and at least one antibody and/or aptamer selected to interact with the immobilization agent and selected to bind with the one or more target biomarkers related to brain injury or disease. The system also includes a signaling agent consisting of an electrochemical impedance signal generated by binding of the antibody and/or aptamer with the one or more target biomarkers related to brain injury or disease; and the bodily fluid sample derived from the patient and in contact with the antibody and/or aptamer. The bodily fluid sample having a presence or an absence of the one or more target biomarkers related to brain injury or disease. Wherein, a change in electrochemical impedance is indicative of the presence of the one or more target biomarkers related to brain injury or disease in the bodily fluid sample. Wherein no change in electrochemical impedance is indicative of the absence of the one or more target biomarkers related to brain injury or disease in the bodily fluid sample.

The conducting material interface may be selected from the group consisting of platinum, gold, iridium, ruthenium, palladium, osmium, and alloys thereof. The conducting material interface may be in a form selected from the group consisting of wire, film, coating, sheet and plate.

In certain embodiments, the conducting material interface includes an epoxy substrate and a multi-array of vertically aligned platinum wires cast in the epoxy substrate.

The bodily fluid sample can be a blood sample. The one or more target biomarkers related to brain injury or disease can be selected from Tau proteins, Glial Fibrilar Acidic Protein (GFAP) and Ubiquitin C-Terminal Hydrolase L1 (UCH-L1). In certain embodiments, the target biomarker is Tau protein.

The antibody and/or aptamer can be conjugated with biotin. The immobilization agent can be selected from the group consisting of avidin, streptavidin, neutravidin and mixtures thereof. The immobilization agent can be applied to a treating agent, and the treating agent can be applied to the surface of the conducting material interface, e.g., the multi-array of vertically aligned conducting material such as platinum wires.

The antibody and/or aptamer is effective to impedimetrically detect simultaneously a plurality of target biomarkers in the bodily fluid sample.

In certain embodiments, the multi-array of vertically aligned conducting material such as platinum wires can be arranged on the surface of the substrate in a concentric configuration.

The antibody and/or aptamer can be effective to impedimetrically detect simultaneously a plurality of the one or more target biomarkers related to brain injury or disease in the bodily fluid sample.

A surface of the conducting material interface, such as an end of the platinum wires, serves as the point of contact for the electrochemical impedance signal to be transduced, allowing for an interpretable reading of output.

In another aspect, the invention includes a method of detecting one or more target biomarkers related to brain injury or disease in a bodily fluid sample of a patient. The method includes obtaining from a patient the bodily fluid sample having a presence or an absence of the one or more target biomarkers related to brain injury or disease; forming a detection device, which includes forming a conducting material interface having a surface; and forming a biological sensor agent, including applying an immobilization agent to the surface of the conducting material interface; selecting an antibody and/or aptamer to selectively bind with the one or more target biomarkers related to brain injury or disease; and interacting the antibody and/or aptamer with the immobilization agent. The method further includes contacting the antibody and/or aptamer with the bodily fluid sample; generating an electrochemical impedance signal as a result of the antibody and/or aptamer binding with the one or more target biomarkers related to brain injury or disease; assessing a presence or an absence of a change in electrochemical impedance; determining the presence of the one or more target biomarkers related to brain injury or disease in the bodily fluid sample due to the change in electrochemical impedance; and determining the absence of the one or more target biomarkers related to brain injury or disease in the bodily fluid sample due to no change in electrochemical impedance.

In certain embodiments, the step of forming a conducting material interface includes providing an epoxy substrate; vertically aligning a multi-array of conducting material such as platinum wires; and casting the multi-array of vertically aligned conducting material such as platinum wires in the epoxy substrate.

The electrochemical impedance signal can be transduced to an interpretable read-out value. The electrochemical impedance signal can also be connected to a hand-held device that is effective to display the read-out value.

The detection device can be in the form of a test strip and the method, can include contacting the bodily fluid sample with the test strip; assessing a visual change to the test strip; correlating the visual change with a chart or key; and based on the correlating, determining if the visual change is indicative of the presence of a change in the electrochemical impedance and the presence of the one or more target biomarkers related to brain injury or disease in the bodily fluid sample. The visual change can also be a color change.

The surface of the conducting material interface can be polished to provide a surface roughness in the range from about 320 grit to about 2400 grit.

DETAILED DESCRIPTION OF THE PREFERRED EMBODIMENTS

The invention relates to multi-array, impedimetric, antibody- and/or aptasensor-based biosensors for the impedimetric detection and screening of one or more target biomarkers of interest, which include Tau proteins, Glial Fibrilar Acidic Protein (GFAP) and Ubiquitin C-Terminal Hydrolase L1 (UCH-L1). The biosensors are effective to detect a single biomarker, or multiple biomarkers simultaneously, present in bodily fluid, such as, blood, that is predictive of the occurrence of concussion and traumatic brain injury (TBI). The risk state of a patient for mild or severe TBI (mTBI or sTBI), as well as concussion state, are determinable at a given time. More particularly, the invention includes an electrochemical assay for electrochemically detecting biomarker concentrations that are present in a minimal amount of blood, e.g., a few drops of blood, by measuring, e.g., quantitatively, impedance changes that occur upon the binding of a target to the antibody- and/or aptamer-based biosensors. The invention includes methods of synthesizing the aptasensors that specifically and selectively bind to an intended target analyte. Furthermore, the invention includes employing the antibodies and/or synthesized aptasensors for detecting and diagnosing brain injury or neurodegenerative diseases. Thus, allowing hospitals and clinicians to treat patients in a more timely and effective fashion. Additionally, the aptasensors can be employed outside of hospitals by non-clinicians, e.g., the patient itself, such that the invention provides a portable, point-of-care system and method for conducting the biosensing, detection and screening.

The antibody- and/or aptamer-based sensors are in-vitro (ex-situ) devices that utilize the bodily fluid sample derived from the patient for impedimetric detection of the one or more target biomarkers of interest. The impedance changes are measured using electrochemical impedance spectroscopy (EIS), which is a highly sensitive, label-free technique that allows for changes in electrochemical impedance resulting from the binding of the target to the antibody and/or aptamer to be transduced into an interpretable read-out value. Thus, the antibody and/or aptamer biosensor electrochemically detects biomarker concentrations present in the minimal amount of blood by measuring the ensuing impedance changes occurring upon the target biomarker binding to the antibody- and/or aptamer-based biosensor.

Biosensors can provide an ultrasensitive method for measuring Tau or other biomarkers in a bodily fluid sample, such as blood, which allows for detection of extremely low levels of Tau or other biomarkers, as well as being minimally invasive. Acquiring a blood sample requires inducing significantly less pain and significantly less effort as compared to the acquisition of a CSF sample. It is an objective to design a highly sensitive biosensor for Tau proteins, GFAP and UCH-L1 on a conducting material interface, using electrochemical impedance spectroscopy as a detection method.

The conducting material interface for use in the invention can be selected from such elements and materials known in the art. Suitable conducting materials include but are not limited to platinum, gold, iridium, ruthenium, palladium, osmium, and alloys thereof. In certain embodiments, platinum is a preferred conducting material. The conducting material such as platinum, with its noble metal status, high electrical conductivity, affinity towards immobilizing agents, and biocompatibility, is ideal for the material interface. Unlike silver, platinum does not oxidize in the ambient air. Further, platinum has a low adsorption, which allows for testing whole blood samples instead of only plasma samples. Numerous other biosensor arrays previously developed required plasma samples. The conducting material interface can be in a variety of forms. Suitable forms include but are not limited to, wire(s), film(s), coating(s), sheet(s) and plate(s). In certain embodiments, the conducting material interface includes vertically aligned platinum wires. One end of the wires can be cast in an epoxy substrate and the other end provides the surface of the conducting material interface.

Furthermore, the use of electrochemical impedance spectroscopy allows for a mode of detection that is miniaturized into a handheld instrument. The use of an impedimetric biosensor for the detection of one or more of Tau proteins, GFAP and UCH-L1 assists with the prognosis of brain injury or neurodegenerative diseases, thereby allows hospitals and clinicians to treat patients in a more timely and effective fashion.

As used in the specification and in the claims, the singular form of "a", "an", and "the" may include plural referents unless the context clearly dictates otherwise.

In general, according to the invention, antibody and/or aptamer are forms of biological detection (sensing) agents that are utilized to detect whether there exists certain analytes/biomarkers within a subject fluid sample. The term "antibody" or "aptamer" as used herein, refers to an oligonucleotide or oligonucleotide chain that has a specific and selective binding affinity for an intended target compound or molecule (e.g., analyte) of interest, and is capable of forming a complex with the intended target compound or molecule of interest. The complexation is target-specific in the sense that other materials which may accompany the target, do not complex to the antibody or aptamer. It is recognized that complexation and affinity are a matter of degree. However, in this context, "target-specific" means that the antibody or aptamer binds to the target with a much higher degree of affinity than it binds to other, e.g., contaminating, materials in a sample. As used herein, the term "binding" refers to an interaction or complexation between the target compound or molecule of interest and the antibody or aptamer. Antibody or aptamer can be used in diagnosis by employing them in specific binding assays for the target compound or molecule of interest.

As used herein, "biomarkers" refer to naturally occurring or synthetic compounds, which are a marker of a disease state or of a normal or pathologic process that occurs in an organism. The term "analyte," as used herein, refers to any substance, including chemical and biological agents that can be measured in an analytical procedure. The term "bodily fluid", as used herein, refers to a mixture of molecules obtained from a patient. Bodily fluids include, but are not limited to, exhaled breath, whole blood, blood plasma, urine, semen, saliva, lymph fluid, meningeal fluid, amniotic fluid, glandular fluid, sputum, feces, sweat, mucous and cerebrospinal fluid. Bodily fluid also includes experimentally separated fractions of all of the preceding solutions or mixtures containing homogenized solid material, such as tissues and biopsy samples. According to the invention, biomarkers and/or analytes are detectable in bodily fluid, such as, but not limited to, a minute volume of blood.

An "array" is an intentionally created collection of molecules. The molecules in the array can be identical or different from each other.

The systems (e.g., biosensors) and methods of the invention can include at least one biological sensor agent and at least one signaling agent wherein the biological sensor agent(s) and signaling agent(s) together provide a means for detecting, signaling, and/or quantifying target compounds of interest in bodily fluids, such as, blood. The biological sensor agent is selected for its ability to specifically and selectively interact with and bind to (only) the target analyte/ biomarker molecules. In accordance with the invention, the biological sensor agent is attached to the surface of a conducting material interface. The biological sensor agent can be introduced by functionalization of the surface of a conducting material interface. The biological sensor agent can be directly attached to the conducting material interface or indirectly attached by employing linker molecules, such as, but not limited to, proteins. As aforementioned, in certain embodiments, the conducting material is a multi-array of vertically aligned conducting material such as platinum wires cast in an epoxy substrate. The biological sensor agent is in the form of an antibody or aptamer. For example, an antibody or aptamer-linked protein can be immobilized on a surface of the conducting material interface. The antibody or aptamer can be conjugated to a signaling agent, e.g., the electrochemical impedance signal. The signaling agent is detectable under preselected conditions, e.g., after antibody or aptamer binding to the analyte/biomarker of interest. In accordance with the invention, signaling is related to a change in impedance, upon binding of the antibody or aptamer with the analyte/biomarker of interest. An end of the conducting material such as platinum wires provides a point of contact for an electrochemical impedance signal to be transduced to an interpretable read-out value.

In certain embodiments, the invention utilizes conducting material such as platinum wire serving as a conducting material interface and platform for a biosensing surface. The immobilized biological sensor agent is applied to the platform. The immobilized biological sensor agent includes the antibody or aptamer, e.g., biotinylated aptamer, and the immobilization agent, e.g., linker. Furthermore, the signaling agent includes the electrochemical impedance signal. The antibody or aptasensor is tailored to detect one or more of various target biomarkers predictive of brain concussion, brain disease or traumatic brain injury, such as Tau proteins, in bodily fluids, primarily, but not limited to, blood. The sample of bodily fluid can be a minute volume, such as, for example, a few drops (e.g., about 1-5 drops) of blood, and the determination can be obtained in a relatively short period of time, such as, for example, about several minutes to five minutes. Furthermore, the detection and screening processes can be conducted in a point-of-care location that is other than a hospital or doctor's office, and by a person other than a trained medical professional.

Known systems for detecting brain concussion or traumatic brain injury include magnetic resonance imaging (MRI), computerized tomography (CT), electrocardiography (ECG) and invasive techniques. For systems focused on blood work, enzyme-linked immunosorbent assays (ELISA) and lateral flow devices (LFD) can be employed. These analyses and devices for detection involve expensive equipment, highly-skilled and trained personnel for proper analysis, associated risks and a significant amount of time for processing, which includes analytical time, e.g., the duration of the assay, and pre-analytical time, involving paperwork, drawing samples, labeling samples and enormous preparation time. In contrast, the multi-array antibody and aptamer biosensors in accordance with the invention provide portable, point-of-care, on-demand devices that can be utilized in the absence of expensive equipment and highly trained professionals to assess levels of one or more target biomarkers, such as Tau proteins, in the blood at the patient's bedside, for example, within a short period of time, such as, several minutes. Since the use of these biosensors do not require professional skill or training, they represent a simple and facile mode of detection.

Further, known impedimetric devices utilize antibodies and enzymes as detection elements, and platinum is used in tandem with other material interfaces such as carbon nanotubes/nanocomposites, graphene, chitosan, silica, polymers, or gold. In contrast, the multi-array antibody and/or aptamer biosensors in accordance with the invention can utilize conducting material, such as platinum, alone as the conducting material interface.

Synthesis of the multi-array biosensors, in accordance with the invention, include the use of appropriate linkers and proteins to immobilize the target biomarker-specific antibody and/or aptamer to the surface of the conducting material. The antibody and/or aptamer is selected based on its capability to interact with the target biomarker. In accordance with certain embodiments of the invention, suitable antibody and/or aptamer include antibodies or aptamers selected specifically for Tau protein. The conducting material is selected, such as vertically aligned, platinum wire arrays embedded in an epoxy mold, e.g., in a circular fashion or pattern, wherein the surface of the epoxy mold is polished, e.g., to approximately 50 nm, for surface exposure. The surface of the conducting material, such as the ends of platinum wire arrays, then can be treated with a thiol-based compound, such as, an aminothiol, including but not limited to, cysteamine and/or glutaraldehyde. An immobilization agent, such as, avidin, is adsorbed thereon. Antibody and/or aptamer can be conjugated with biotin. The biotinylated antibody and/or aptamer for the above-described target markers interact with the immobilization agent to develop the biosensing surface. Application of the treating agent and the immobilization agent, and interaction of the biotinylated antibody and/or aptamer can be carried out in a sequential manner, to develop the biosensing surface. The presence of the selected biomolecule, e.g., biotinylated antibody and/or aptamer, provides for the detection of the target biomarker, e.g., Tau protein. As previously described, antibodies and aptamers are oligonucleotide sequences that are highly specific for their designated antigen. However, unlike antibodies, aptamers can undergo denaturation and renaturation. The aptamer biosensors can therefore be regenerated in the presence of certain solvents, thus providing a reusable and regenerative sensor platform for potentially continuous use rather than one-time detection (as in commercially known glucose sensors). Thus, generally, aptamers are more robust platforms with a longer shelf-life and more importantly, allowing for aptamer biosensors to be reusable rather than only a one-time, single-use assay.

In general, an electrochemical sensor can be used to measure a change in output of a sensing element caused by chemical interaction of a target marker on a sensing element. In accordance with the invention, electrochemical impedance spectroscopy (EIS) is the technique utilized to characterize the surface of an aptasensor at various stages of development. EIS is a highly sensitive and label-free technique that allows for changes in electrochemical impedance resulting from the binding of the aptamer to the antigen, e.g., target marker. The electrochemical impedance can be transduced to a read-out value. Thus, the aptasensor is capable of electrochemically detecting target biomarker concentrations that are present in a minimal amount of blood by measuring the impedance changes that occur upon the binding of antigens to the aptasensor. The impedimetric detection of the target biomarker can be performed within minutes, and the aptasensor can be reused for this purpose multiple times.

In accordance with the invention, modified conducting material, such as vertically aligned platinum wire-based antibody and/or aptamer biosensors are provided for the impedimetric detection of one biomarker or the simultaneous detection of more than one biomarker of interest. In certain embodiments, the antibody and/or aptamer biosensors are synthesized by casting upright conducting material such as platinum wires in epoxy, in various configurations and patterns. In certain embodiments, the wires are cast in a circular pattern. The diameter of the wires may vary and can range from about 0.25 mm to about 1.0 mm. In certain embodiments, the diameter is about 0.25 mm or about 0.5 mm or about 1.0 mm.

The conducting material interface is used for functionalization and establishing electrical connection. The surface of the conducting material interface has an immobilized antibody and/or aptamer attached thereto. In certain embodiments, one end of the wire is cast in epoxy and the opposite end has the immobilized antibody and/or aptamer attached thereto and, in this embodiment, the wires are utilized for functionalization and establishing electrical connection.

The resulting conducting material, such as platinum, electrodes are polished using polishing media, such as, but not limited to, silicon carbide (SiC), to various different grits and functionalized to bind the target biomarker-specific antibodies and/or aptamers to the surface. The surface roughness can vary and, for example, the polishing grit size, can range from about 320 grit (e.g., about 50 µm) to about 2400 grit (e.g., about 50 nm). In certain embodiments, the grit size is about 320 grit or about 1200 grit (e.g., about 5 µm) or about 2400 grit. It is contemplated and understood that the impedimetric devices can be tested against various clinically relevant concentrations of target biomarker to determine the ideal wire diameter and polishing grit.

In certain embodiments of the invention, the antibody and/or aptamer biosensors utilize 0.5 mm-diameter wires polished to about 1200 grit (e.g., 5 µm) size.

Electrochemical impedance spectroscopy (EIS) can be employed as a mode of impedimetric detection for the one or more target biomarkers.

Impedimetric biosensors according to the invention provide one or more of the following features and advantages as compared with known biosensors: highly sensitive, low cost, allow for rapid analysis and miniaturization, and label-free, thus significantly reducing the complexity of biosensor development.

There are various conventional mechanisms for functionalizing, e.g., attaching an antibody and/or aptamer thereto, the conducting material interface, e.g., platinum wires, including, but not limited to, adsorbing a binding material thereon. The binding material is selected based on its capability to bind particular antibody and/or aptamer. Non-limiting examples of suitable binder materials include avidin, streptavidin, and neutravidin. In certain embodiments, neutravidin is preferred. Further, the antibody and/or aptamer for binding to the avidin is selected based on its capability to interact with the one or more target biomarkers. Non-limiting examples of suitable antibody and aptamer include biotinylated antibody and aptamer selected specifically for target biomarkers, such as, but not limited to, those described herein. Thus, the avidin is immobilized on the surface of the conducting material and the biotinylated antibody and/or aptamer attaches to the avidin.

The process of biotinylation generally includes covalently attaching biotin to a protein, nuclei acid or other molecule. Biotin is known to bind to avidin with high affinity. The antibody and/or aptamer can be biotinylated chemically or enzymatically using conventional processes and apparatus.

In certain embodiments, the multi-array of conducting material such as platinum wires is embedded in an epoxy substrate, the surface of the epoxy substrate is polished and the wires on the surface of the epoxy substrate are treated with avidin followed by biotinylated antibody and/or aptamer. In certain embodiments, the biotinylated antibody and/or aptamer is selected based on its ability to interact with Tau protein biomarkers or other biomarkers, such as GFAP and UCH-L1. These target biomarkers are released into bodily fluids, e.g., blood.

In certain embodiments, the biosensor according to the invention includes (i) an analyte, e.g., TBI protein, (ii) a biological detection element, e.g., Tau antibody, (iii) a biomaterial interface, e.g., platinum wire electrodes, (iv) a transducer, e.g., EIS, and a signal to (v) a measuring device, e.g., potentiostat.

In certain embodiments, the biosensor functionalization includes cysteamine and/or glutaraldehyde, followed by avidin, followed by antibody and followed by antigen.

The biosensors developed in accordance with the invention may function as ex-situ biosensors. A portable (e.g., point-of-care, on-demand) device, such as, a handheld device, may be developed. There are various mechanisms that are known in the art to produce a handheld device that may be employed with the biosensors, and are suitable for use with the biosensors of the invention. In certain embodiments, the electrochemical impedance signal is transduced to a read-out value, and the read-out value is displayed on a handheld device. The handheld device can be an electronic device, such as but not limited to a smart telephone, tablet or the like. Alternatively, the handheld device can include, for example, a test strip similar to conventional glucose sensors which are known in the art, composed of paper or like material. There is typically a corresponding standard chart or key used to interpret the results displayed on the test strip. In these embodiments, the test strip is contacted with a patient bodily fluid sample, such as by applying the sample, e.g., a few drops, to the test strip or by dipping/immersing the test strip into the bodily fluid sample. The test strip is then visually observed or inspected to determine whether there is a visible change, such as a change in color, based on its contact with the sample. The mere presence of a visual change, such as color change, is indicative of a change of electrochemical impedance, e.g., binding of the antibody and/or aptamer in the test strip with the one or more target biomarkers, e.g., Tau protein, in the bodily fluid sample, and therefore, the presence in the sample of the one or more target biomarkers of interest. Further, the corresponding key or chart can include varying degrees or intensity of change. The degree or intensity of visual change on the test strip is correlated to a particular quantitative amount of the electrochemical change and corresponding level of target biomarker(s) of interest in the sample. Similarly, the absence of a visual change on the test strip is indicative of the absence of the target biomarker(s) of interest in the patient bodily fluid sample.

For example, in accordance with certain embodiments of the invention, a bodily fluid sample, such as blood, is obtained or removed from a patient. Further, the sample can be obtained or removed by the patient. At least a portion of the sample is deposited on the test strip and within a time period, e.g., seconds or a few minutes, a change in color of at least a portion of the test strip is visually observed based on the target biomarker(s) in the sample interacting with the test strip, e.g., biosensor. The particular color and/or the intensity of the color change is compared and matched with a key to determine the level of the target biomarker(s), e.g., Tau protein, in the sample. Based on the visible change of the biosensor, the presence or absence or particular concentration of the target biomarker(s) is determined efficiently and accurately. The response time may be in minutes or even seconds, and the results can be obtained by the patient in a domestic setting, without the need for medical personnel, laboratory equipment and a medical facility.

Therefore, impedimetric biosensors in accordance with the invention are ideal portable, e.g., point-of-care, on-demand, diagnostics that can be used, for example, at the bedside, in ambulances, or even during clinical visits as a useful screening device for the detection of target biomarkers and therefore, the diagnosis of brain concussion, brain disease, traumatic brain injury and neurodegenerative disease.

Further, in accordance with the invention, impedimetric biosensors exhibiting the following attributes are provided: (i) re-usable aptamer-based electrochemical assay; (ii) multiple target biomarker detection in a single setting; and (iii) amenable to hand-held model translation.

Point-of-care handheld antibody and/or aptamer biosensors in accordance with the invention allow patients to frequently detect and measure their target biomarkers. These biosensors are inexpensive, e.g., comparable in price to blood-based glucose biosensors that are currently commercially available. Further, existing insurance codes for glucose biosensors and target biomarker testing could be readily applied to antibody and/or aptamer biosensors for full or partial reimbursement of the cost. Thus, patients can affordably, routinely and rapidly detect and measure their target biomarkers.

In an emergency room setting, significant minimization of turn-around time may be realized, resulting in more efficient allocation of resources and providing more effective care for patients. For example, decreasing the time of diagnosis can reduce the time required to make an admission decision and therefore, ensure administration of rapid care to the patient. In addition, decreasing the time of diagnosis may also ensure that patients suffering from less severe conditions are not allocated more expensive, redundant resources.

In certain embodiments, these biosensors can be tailored with a wireless chip to allow for wireless transmission of biomarker levels to a patient's electronic health records. Thus, reducing the amount of paperwork necessary and allowing the physician to directly view trends in the levels of biomarkers and detecting early a precarious patient situation.

It should be understood that the embodiments described herein and the examples provided below are for illustrative purposes only and that various modifications or changes in light thereof will be suggested to persons skilled in the art and are to be included within the spirit and purview of this application.

Examples

In accordance with the invention, impedimetric vertically-aligned platinum wire-based antibody and/or aptamer biosensors for the detection of brain concussion and traumatic brain injury were developed and parameter assessment was conducted. Upright platinum wires of varying diameters were cast in epoxy such that one end was utilized for functionalization and the other end was used to establish electrical connection. The resulting platinum electrodes were accordingly polished to various different grits, functionalized to bind the Tau-specific antibody and/or aptamer to the surface, and tested against various clinically relevant concentrations to determine the ideal parameters for biosensor and medical device development.

Methods and Materials

Platinum electrodes were fabricated by casting upright platinum wires in epoxy in a concentric pattern to form a disk containing multiple electrodes (referred to as a multi-array electrode disk). Platinum wires were polished to 1200 grit (5 μm), sonicated in DI Water, and then functionalized with cysteamine (20 mg/mL) to form a transition metal thiolate complex on the platinum surface, thus making the surface more amenable to protein binding. The disk was then functionalized with glutaraldehyde (5% w/v), during which one of the aldehyde groups of glutaraldehyde bonded to the amine group in cysteamine, and the other remained exposed for protein binding. The disk was then functionalized with NeutrAvidin (1 mg/mL), a multimeric protein with 4 binding sites to increase the amount of antibody that could be bound to the surface. Lastly, the disk was treated with biotinylated Tau antibody, wherein the biotin would bind to the available sites on the NeutrAvidin. All the binding steps were performed at room temperature in a dark enclosure to ensure minimal exposure to light and ambient air. After completion of the biosensor preparation, 2 μl of various concentrations of Tau protein were bound in succession to the electrodes (5 minutes for each concentration) and the biosensors were tested after each concentration binding step. Note, 2 μl of protein was used, whereas conventional assays use 25 μl or higher for each assay. Therefore, the developed biosensor is not only designed to be more sensitive than current arrays, but also requires extremely small volumes of samples, and requires very little time (less than 10 minutes for antigen binding and detection).

All the electrochemical biosensor testing was performed in a 5 mM ferro/ferricyanide electrolyte ($Fe(CN)_6^{3-/4-}$) prepared in 10 mM phosphate buffered saline (PBS). The electrochemical cell consisted of the electrode disk as the working electrode, a silver wire as the reference electrode, and a platinum wire as the counter electrode. These were run for 5-minute at open circuit potentials to ensure the stability of the biosensor, and then electrochemical impedance spectroscopy ranging from 10,000 Hz-0.1 Hz was performed for each binding step. After each, proteins were removed from the surface.

Results & Discussion

The first Tau detection experiments were performed in a concentration range of 50 pg/mL-5000 pg/mL, which is a rather high level of Tau protein (levels can range from 100-500 pg/mL in CSF, and lower in circulating blood), and were performed to determine the ideal concentration of Tau antibody necessary for enhanced detection of Tau protein. It was demonstrated that the highest concentration of antibody led to the highest slope (thus demonstrating increased sensitivity), extremely good correlation between an increase in impedance and concentration, and had narrow margins of error. Therefore, all the subsequent experiments were performed with 100 μg/mL antibody for the antibody binding step. At higher concentrations, the biosensor experienced saturation. One reason for this saturation may be that the concentrations chosen for this experiment were rather high, e.g., higher than what is usually seen even in CSF. Another reason may be the successive testing of concentrations—if each electrode was used to test one concentration (which would occur during clinical testing) instead of all concentrations (as demonstrated here), this saturation effect may not be observed, especially at the clinically relevant concentrations.

In subsequent examinations, experiments were conducted to determine what was the lower limit of detection for the biosensor, and to try to avoid saturation, the concentration set was divided into two—a set of concentrations ranging from 0.001-10 pg/mL, and a set of concentrations ranging from 0.005-50 pg/mL. For both concentration sets, a drop in the slope value was observed (implying a drop in sensitivity), compared to the calibration curves for the higher concentration set. This was expected because sensitivity begins to diminish as the biosensor attempts to detect lower concentrations until reaching its lower limit of detection. However, there was excellent correlation between the change in charge transfer resistance (impedance) and the increase in concentration, and there was a very small error margin for the 0.001-10 pg/mL concentration set. The error margin was much larger for the 0.005-50 pg/mL concentration set, which may be explained by the higher concentrations, which could lead to saturation quicker and thus increase the variability of the biosensor response. Nevertheless, at each concentration the biosensor response was significantly different and is therefore acceptable. However, despite going to lower concentration ranges, logarithmic calibration curves were observed, implying saturation of the biosensor occurs even at very low concentrations. This saturation, even at lower concentration ranges, supports the theory that the biosensors were saturating due to the successive concentration binding. Therefore, if eight biosensors were tested and one specific concentration was bound to each electrode, and the response generated from each electrode was compared, a more desired linear response may be observed. Nevertheless, the biosensors demonstrated that they were successfully able to detect concentrations of Tau protein within acceptable error margins, and that the biosensors were extremely sensitive, capable of detecting Tau concentrations as low as 0.001 pg/mL.

CONCLUSIONS

In summary, there was designed a simplistic platinum based biosensor that allowed for the detection of Tau protein through the use of electrochemical impedance spectroscopy. This simplistic design required no labeling and once scaled down and miniaturized, the integration required no expensive instrumentation, thereby making it portable and cost-effective. In addition, the biosensor was highly sensitive at detecting extremely low concentrations of Tau protein, therefore ensuring that even minimal fluctuations in Tau were detected by the biosensor. The biosensor may be useful for monitoring the progression of brain injuries (especially in sports) or neurodegenerative diseases (especially Alzheimer's). Additional experimentation with Tau and other TBI biomarkers, such as GFAP and UCH-L1, is required to ensure that the biosensors consistently demonstrate a linear rather than logarithmic response, and that this response will not be affected by the cells and proteins present in whole blood. These initial results are nevertheless, very promising and demonstrate the possibility of developing a biosensor for detection of Tau in blood samples to effectively treat brain injury and neurodegenerative diseases.

The invention claimed is:

1. A portable, ex-situ system to impedimetrically detect one or more target biomarkers related to brain injury or disease in a bodily fluid sample of a patient, comprising:
    a conducting material interface, comprising:
        an epoxy resin; and
        a multi-array of vertically aligned conducting metal wires selected from the group consisting of platinum wires, gold wires, iridium wires, ruthenium wires, palladium wires, osmium wires, and alloys and combinations thereof, each of the plurality of conducting metal wires having a first end and an opposite second end with the first end cast in the epoxy resin;
    a thiol-based compound applied to the second end of the plurality of conducting wires to form a thiol treated surface;
    an immobilization agent applied to the thiol treated surface; and
    at least one biotinylated antibody and/or aptamer applied to the immobilization agent, selected to bind with the immobilization agent and the one or more target biomarkers related to brain injury or disease;
    a signaling agent comprising an electrochemical impedance signal generated by binding of the at least one biotinylated antibody and/or aptamer with the one or more target biomarkers related to brain injury or disease; and
    the bodily fluid sample derived from the patient and in contact with the at least one biotinylated antibody and/or aptamer to detect the one or more target biomarkers related to brain injury or disease,
    wherein the system is structured such that in its use a change in electrochemical impedance indicates a presence of the one or more target biomarkers related to brain injury or disease in the bodily fluid sample and binding of the at least one biotinylated antibody and/or aptamer with the one or more target biomarkers in the bodily fluid sample, and
    wherein the system is structured such that in its use an absence of a change in electrochemical impedance indicates an absence of the one or more target biomarkers related to brain injury or disease in the bodily fluid sample.

2. The system of claim 1, wherein the bodily fluid sample is a blood sample.

3. The system of claim 1, wherein the one or more target biomarkers related to brain injury or disease are selected from the group consisting of Tau proteins, Glial Fibrilar Acidic Protein (GFAP) and Ubiquitin C-Terminal Hydrolase L1 (UCH-L1).

4. The system of claim 1, wherein the immobilization agent is selected from the group consisting of avidin, streptavidin, neutravidin and mixtures thereof.

5. The system of claim 1, wherein the antibody and/or aptamer sensor is effective to impedimetrically detect simultaneously a plurality of target biomarkers related to brain injury or disease in the bodily fluid sample.

6. The system of claim 1, wherein the multi-array of vertically aligned conducting material wires are arranged in a concentric configuration.

* * * * *